(12) United States Patent
Lonigro et al.

(10) Patent No.: US 8,467,064 B2
(45) Date of Patent: Jun. 18, 2013

(54) GAS SAMPLING DEVICE

(75) Inventors: Lucien Lonigro, Aix les Milles (FR); Pierre Cholat, Meyrargues (FR)

(73) Assignee: AP2E (FR)

(*) Notice: Subject to any disclaimer, the term of this patent is extended or adjusted under 35 U.S.C. 154(b) by 45 days.

(21) Appl. No.: 13/114,093

(22) Filed: May 24, 2011

(65) Prior Publication Data

US 2012/0133942 A1     May 31, 2012

Related U.S. Application Data

(63) Continuation of application No. PCT/FR2009/001333, filed on Nov. 20, 2009.

(30) Foreign Application Priority Data

Nov. 24, 2008 (FR) ...................................... 08 06593

(51) Int. Cl.
*G01N 21/00* (2006.01)
(52) U.S. Cl.
USPC ......................................................... 356/437
(58) Field of Classification Search
USPC 356/301, 437, 454; 381/9, 32, 92; 73/863.84, 73/864.81; 250/227.23
See application file for complete search history.

(56) References Cited

U.S. PATENT DOCUMENTS

| 6,284,547 | B1 | 9/2001 | Schafer |
| 7,057,175 | B2* | 6/2006 | Namose .................. 250/339.13 |
| 2005/0073687 | A1* | 4/2005 | Morville et al. ............... 356/437 |
| 2008/0060455 | A1 | 3/2008 | Coyle |

FOREIGN PATENT DOCUMENTS

| DE | 277378 A3 | 4/1990 |
| EP | 0194955 A1 | 9/1986 |
| WO | WO-99/57542 A1 | 11/1999 |
| WO | WO-03/031949 A1 | 4/2003 |

OTHER PUBLICATIONS

"International Application No. PCT/FR2009/001333, International Preliminary Report on Patentability issued Mar. 18, 2011 [with English Translation]", (Mar. 18, 2011), 12 pgs.
"International Application No. PCT/FR2009/001333, International Search Report and Written Opinion issued Mar. 26, 2010 [with English translation of Search Report]", (Mar. 26, 2010), 16 pgs.

* cited by examiner

*Primary Examiner* — Gregory J Toatley
*Assistant Examiner* — Dominic J Bologna
(74) *Attorney, Agent, or Firm* — Schwegman, Lundberg & Woessner, P.A.

(57) ABSTRACT

The invention relates to a gas sampling device comprising a probe for sampling gas, an exploiting device for exploiting the gases sampled, a pipe for transmitting the gases sampled by the probe to the exploiting device, and means for lowering the pressure of the gases sampled in the pipe, to lower the dew point of the gases sampled, the means for lowering the pressure comprising an expansion nozzle arranged in the probe and communicating with the pipe, and a suction device for sucking the gases sampled in the pipe through the exploiting device. Application of the invention to the analysis of hot gases loaded with water vapor.

15 Claims, 1 Drawing Sheet

GAS SAMPLING DEVICE

CLAIM OF PRIORITY

This application is a continuation under 35 U.S.C. 111(a) and claims the benefit of priority under 35 U.S.C. §120 to International Patent Application No. PCT/FR2009/001333, filed on Nov. 20, 2009, and published on May 27, 2010, as WO 2010/058107A1, which claims the benefit under 35 U.S.C. 119(e) to French Patent Application Serial No. 08 06593, filed on Nov. 24, 2008, the benefit of priority of each of which is claimed hereby, and each of which are incorporated by reference herein in their entirety.

FIELD OF THE INVENTION

The present invention relates to gas sampling, and in particular industrial gases, particularly with a view of carrying out an analysis of their compositions. The present invention applies in particular, to the analysis of hot and wet gases, particularly in chemical or petrochemical installations, cement plants, steelmaking plants, incinerators, or gas process or production installations.

BACKGROUND OF THE INVENTION

A sampling device generally comprises a probe for sampling gas and a pipe for transmitting the gas samples taken to a system for exploiting samples, such as a gas analyzer.

Generally, gas sampling with a view of analyzing their compositions, constitutes a key step, in particular when the gases to be sampled are hot and comprise a high proportion of water in the form of vapor. In this context, it is indeed sensitive to perform reliable analyses, and current sampling devices require frequent maintenance operations.

In particular, sampling hot and wet gases raises a condensation issue. Indeed, the dew point, also called "condensation temperature" of the water contained in hot gases having a high rate of water vapor can reach several dozens, even several hundreds of degrees Celsius. The result is that at ambient temperature, the water vapor contained in these gases may condensate in droplets which deposit onto the walls in contact with the gases. If the gases sampled comprise molecules soluble in water, the molecules tend to be caught and to dissolve in the droplets. The result is that the compositions of the gases which are transmitted to the exploiting device do not correspond to the compositions of the gases sampled. The gas sampling device may therefore affect the compositions of the gases sampled and therefore the quality of the measurements taken if the system which exploits the samples of gases sampled is a gas analyzer. In addition, the droplets formed on walls may cause corrosion phenomena, and all the more since the droplets may be acid due to gas molecules which are dissolved therein. The gas sampling device may therefore also affect the operating costs and conditions of the system into which it is integrated.

Some gas sampling devices are designed to maintain the gases sampled at a temperature higher than the dew point of the water vapor contained in the gases sampled, both in the probe and the pipe. Thus, some of these devices are designed to maintain the sample of gases sampled at a temperature which can reach one or two hundred degrees Celsius. Such devices therefore have a high manufacturing cost, due in particular to the complexity of the pipe which must be heated and the necessary presence of temperature regulators, also high operating and maintenance costs due in particular to the energy required to maintain the device at a relatively high temperature. In addition, these devices imply that the exploitation system is also designed to operate at the same temperature.

Other sampling devices comprise a heated probe and a device for drying the gas sample taken. Such a drying device implements membranes, or a cooling means. These devices also have high manufacturing and maintenance costs due to the presence of the drying device which may require frequent maintenance operations with some gases to be sampled. In addition, these devices denature the sample taken, since they modify the composition thereof.

Other sampling devices provide to dilute the sample taken in another gas, such as dust free air. To that end, these devices comprise a probe which is not necessarily heated, a Venturi system performing sucking and diluting the gas samples, a not heated pipe and a system supplying the dilution gas under pressure at high flow. These devices also have the drawback of denaturing the sample taken since its composition is also modified due to its dilution in another gas, and all the more since the dilution gas may in addition bring impurities. In addition, if the sampling device is linked to an analyzing device, the latter must be very sensitive to be able to detect low quantities of gaseous components due to the dilution.

It is therefore desirable to be able to take gas samples without condensation phenomenon, but without denaturing them or without needing to maintain them at high temperature, to dry them, or to dilute them.

SUMMARY OF THE INVENTION

An embodiment discloses a method of sampling gas comprising sampling gas by a probe and transmitting the gases sampled by means of a pipe to a gas exploiting device using the sampled gases. According to an embodiment the method comprises lowering the pressure of the gases sampled in the pipe, to lower the dew point of the gases sampled therein, lowering the pressure of the gases sampled being performed by sampling the gases through an expansion nozzle arranged in the probe, and by sucking the gases sampled in the pipe through the exploiting device.

According to an embodiment, lowering the pressure of the gases sampled is performed so as to maintain the pressure of the gases circulating in the pipe lower than a value such that the temperature of the gases in the pipe remains higher than the dew point of the gases in the pipe, considering the temperature of the pipe.

According to an embodiment, the method comprises adjusting the suction power of the gases sampled through the calibrated expansion nozzle of sonic type, at a value such that the pressure of the gases sampled circulating in the pipe remains lower than a third of the pressure of the gases sampled upstream from the expansion nozzle, considering variations of the suction power in the absence of regulation.

According to an embodiment, the method comprises regulating the suction power of the gases sampled to maintain the pressure in the pipe substantially constant.

According to an embodiment, the method comprises filtering the gases sampled to extract solid particles susceptible of being present in the gases sampled, before lowering the pressure.

According to an embodiment, the method comprises comprising heating the pipe to maintain the temperature of the pipe above the dew point of the gases sampled.

An embodiment discloses a device for sampling gas comprising a probe for sampling gas, an exploiting device for exploiting the gases sampled and a pipe for transmitting the gases sampled by the probe to the exploiting device. According to an embodiment, the device comprises means for lowering the pressure of the gases sampled in the pipe, to lower the dew point of the gases sampled, the means for lowering the pressure comprising an expansion nozzle arranged in the probe and communicating with the pipe, and a suction device for sucking the gases sampled in the pipe through the exploiting device.

According to an embodiment, the means for lowering the pressure of the gases sampled are configured so as to maintain the pressure of the gases in the pipe lower than a value such that the temperature of the gases in the pipe remains higher than the dew point of the gases in the pipe, considering the temperature of the pipe.

According to an embodiment, the expansion nozzle is a sonic nozzle.

According to an embodiment, the suction device has a suction power higher than a value such that the pressure of the gases sampled circulating of the pipe remains lower than the third of the pressure of the gases sampled upstream from the expansion nozzle, considering variations of the suction power in the absence of regulation of the suction device.

According to an embodiment, the device comprises means for regulating the suction power of the suction device for sucking the gases sampled to maintain the pressure in the pipe substantially constant.

According to an embodiment, the probe comprises a filter for extracting solid particles susceptible of being present in the gases sampled.

According to an embodiment, the device comprises heating means for increasing the temperature in the pipe above the dew point of the gases sampled.

According to an embodiment, the suction device comprises a pump linked to the exploiting device through a pipe, so as to suck the gases in the pipe.

An embodiment discloses a gas analyzing system comprising a sampling device as above-disclosed, the exploiting device comprising a low pressure gas analyzer of the type based on cavity ring-down spectroscopy.

BRIEF DESCRIPTION OF THE FIGURES

Embodiments of the invention will be described hereinafter, in relation with, but not limited to the appended figures wherein.

DETAILED DESCRIPTION OF THE INVENTION

Figure 1:
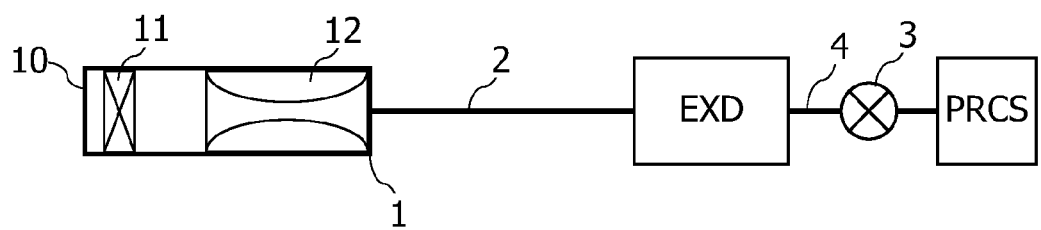
FIG. 1 schematically shows a gas sampling device according to one embodiment, coupled to a gas sample exploiting device, FIG. 2 schematically shows a gas sampling device according to another embodiment, coupled to a gas sample exploiting device.

FIG. 1 shows a gas sampling device comprising a probe 1 and a pipe 2 linking the probe to a gas sample exploiting device EXD. The device EXD is linked to a suction device 3 such as a pump, through a pipe 4 communicating with the pipe 2 through the device EXD. Thus, the suction device sucks gas sampled by the probe 1. The suction device 3 is linked to a process and/or evacuation device PRCS for processing and/or evacuating the gases sampled.

The probe 1 comprises a gas input 10, a filter 11 for filtering out solid particles possibly present in the gases entering the probe through the input 10, and an expansion nozzle 12 such as a section of capillary tube, receiving the gases processed by the filter 11 and which output is linked to the pipe 2. The combination of the suction device 3 and the expansion nozzle 12 allows a pressure, lower than the pressure of the gases at the input 10 of the probe 1, to be obtained in the pipes 2, 4 and in the device EXD. The suction device may be associated to regulation means to maintain at a setpoint value the pressure in the pipe 2 and in the exploiting device EXD.

According to one embodiment, the features of the nozzle 12 and the suction device 3 are chosen to lower the gas pressure in the pipes 2, 4 and in the device EXD, so as to lower the dew points of the gases sampled by the probe 1.

According to one embodiment, the pressure in the pipes 2, 4 and in the device EXD is maintained below a value such that the temperature of the pipes 2, 4 and of the device EXD remains higher than the highest dew point of the gases in the pipes 2, 4 and in the device EXD. In the target applications, the gases sampled generally comprise water vapor and therefore the highest dew point of the gases sampled is that of water.

Thus, the gases in the pipes 2, 4 and in the device EXD cannot condensate. It is thus not necessary to heat the pipes 2, 4 and the device EXD, or to dilute the gases, or to dry them. Therefore, the gases sampled are not denatured. In addition, due to their low pressure in relation to atmospherical pressure, the gases sampled may circulate rapidly in the pipes 2, 4. The result is that the gases sampled are not much in contact with the pipes. The probe 1 and the device for carrying the gases sampled consisting of the pipes 2, 4 and the suction device also have the advantage of being significantly simpler than those of prior art. The result is that the sampling device has manufacturing, operating and maintenance costs significantly lower than the sampling devices of prior art.

The nozzle 12 is for example a calibrated nozzle of sonic type which guarantees a constant gas flow when the following condition is respected:

$$P1-P2>2P2 \qquad (1)$$

where P1 is the pressure of the gases sampled upstream (given the direction of the gas flow in the nozzle), and P2 is the pressure of the gases sampled downstream from the nozzle. When the condition (1) is respected, the flow velocity of the gases in the straight part of the minimum gas passing section in the nozzle reaches the sound speed in these gases. In other words, the condition (1) is respected when the pressure in the pipe 2 is lower than the third of the pressure upstream from the nozzle 12. Consequently, as long as the pressure in the pipe 2 respects the condition (1), it is independent of the suction power of the device 3.

The suction power of the suction device 3 may be adjusted so as to always respect the condition (1) even if it is subjected to variations linked to the technology used to make the suction device, in the absence of regulation. That way, the gas flow in the pipes 2, 4 is constant and can be determined with precision, without needing to regulate the suction power. Being a purely static element, the nozzle 12 also has the advantage of not requiring maintenance operations if it is made of inert materials in relation to the gases susceptible of being sampled by the probe 1.

It is to be noted that the gas expansion generally causes a cooling of the gases sampled. If the temperature of the gases to be sampled, i.e. of the probe 1 is higher than the ambient temperature of the pipe 2 and of the exploiting device EXD, the gases cooled by expansion are heated by the probe. Thus, the temperature drop resulting from the gas expansion is at least partially compensated by the ambient temperature of the probe. If the gases to be sampled are at the ambient temperature of the pipe 2 and the exploiting device EXD, the dew point is lower than the ambient temperature. The pressure drop to be made is therefore low, so that the temperature drop resulting from the gas expansion is also low.

It may happen that it is not possible to reach a pressure in the pipe which is low enough to avoid the condensation of the gases sampled, considering the admissible suction power or considering a minimum pressure required to exploit the gases sampled. This situation may happen when the gases to be sampled are very hot and very wet, so that the dew point of the gases is very high, and the ambient temperature of the pipe 2 is low. The pipes 2 and 4 and the exploiting device EXD may then be associated to means such as a thermal isolation, or heating means, to maintain them at a temperature higher than the dew point of the gases sampled.

Figure 2:
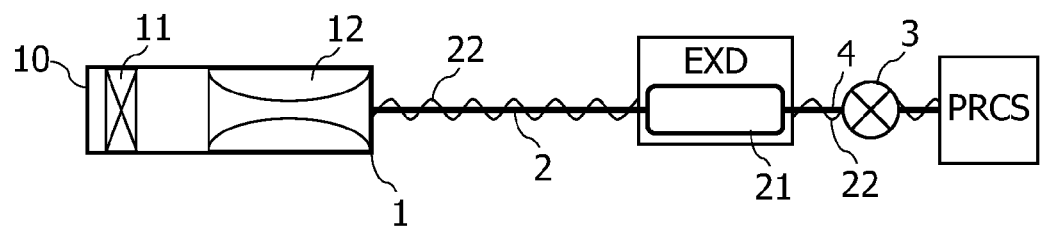

Thus, FIG. 2 shows a sampling device which differs from that of FIG. 1 in that the pipes 2 and 4 are equipped with heating means 22, and in that the exploiting device EXD comprises a heated chamber 21 in which the gases sampled circulate.

It is to be noted that the heating means 22 cannot be compared to the heating means which are required in the devices of prior art transmitting the gases sampled at atmospherical pressure, since the dew point of the gases sampled has been lowered in a way which may be significant, by the nozzle 12 combined to the suction device 3. Indeed, in some applications, the heating means required in prior art must be able to bring the pipe to a temperature which can reach two hundred degrees Celsius, whereas the heating means 22 which could be necessary in the sampling device of FIG. 2 must be able to bring the pipes 2, 4 to a maximum temperature of one or two dozens of degrees Celsius.

The exploiting device EXD comprises for example a gas analysis device, and/or a device for performing mixing with other gases.

In one embodiment, the exploiting device EXD comprises a low pressure gas analyzer based on a cavity ring-down spectroscopy. Such an analyzer is for example described in the patent applications WO9957542 (also published under the number U.S. Pat. No. 6,504,145), and WO 2003/031949 (also published under the number U.S. Pat. No. 7,450,240). Such an analyzer comprises a resonant optical cavity in which the gases sampled circulate, a laser source such as a laser diode, supplying a laser beam which wavelength is adjustable, which is sent into the resonant cavity. The light going out of the resonant cavity is received by a photodetector, the signal supplied by the photodetector being analyzed by a signal analysis circuit. The laser beam is applied to the cavity during periods of adjustable durations, so that between the emission periods of the laser beam, the photons trapped in the cavity are subjected to exponential decay as a function of time. If the cavity is empty, or if the wavelength of the photons is outside an absorption pipe of a gas located in the cavity, the decrease of photons trapped in the cavity has a certain time constant depending mainly on losses introduced by the minors making the resonant cavity. This time constant is reduced if the absorption spectrum of a gas present in the cavity comprises an absorption pipe at the wavelength of the photons trapped in the cavity.

It will appear clearly to those skilled in the art that the present invention is susceptible of various embodiments. In particular, the invention is not limited to a device for lowering pressure comprising an expansion nozzle and a suction pump. Thus the pump may be replaced by a vacuum source, such as spatial vacuum if the sampling device is intended to equip a spacecraft, or a depression source, for example if the gases to be sampled by the probe are at a pressure higher than atmospherical pressure.

The invention claimed is:

1. A method of sampling gases comprising:
   sampling gases by a probe,
   transmitting all and only the sampled gases by the probe to a gas exploiting device through a pipe connecting the probe to the exploiting device, and
   lowering the pressure of the sampled gases in the pipe and the exploiting device, to lower the dew point of the sampled gases therein to a value lower than the temperature of the pipe and the exploiting device, lowering the pressure of the sampled gases being performed by sucking the sampled gases through an expansion nozzle arranged in the probe, and by sucking the sampled gases in the pipe and in the exploiting device by means of a sucking source connected to the exploiting device downstream from the exploiting device.

2. The method according to claim 1, wherein lowering the pressure of the sampled gases is performed so as to maintain the pressure of the gases circulating in the pipe lower than a value such that the temperature of the gases in the pipe remains higher than the dew point of the gases in the pipe, considering the temperature of the pipe.

3. The method according to claim 1, comprising adjusting a suction power applied to the sampled gases by the suction source through the calibrated expansion nozzle of sonic type, at a value such that the pressure of the sampled gases circulating in the pipe remains lower than one third of the pressure of the sampled gases upstream from the expansion nozzle, considering variations of the suction power when the suction power is not regulated.

4. The method according to claim 1, comprising regulating the suction power of the sampled gases to maintain the pressure in the pipe substantially constant.

5. The method according to claim 1, comprising filtering the sampled gases to extract solid particles susceptible of being present in the sampled gases, before lowering the pressure.

6. The method according to claim 1, comprising heating the pipe to maintain the temperature of the pipe above the dew point of the sampled gases.

7. A device for sampling gases comprising:
   a probe for sampling gases,
   an exploiting device for exploiting the sampled gases,
   a pipe connecting the probe to the exploiting device, for transmitting all and only the sampled gases from by the probe to the exploiting device,
   an expansion nozzle arranged in the probe and communicating with the pipe, and
   a suction source connected to the exploiting device downstream from the exploiting device, for sucking the sampled gases in the pipe through the exploiting device, the expansion nozzle and the suction device being configured to lower the pressure of the gases sampled in the pipe, to lower the dew point of the sampled gases, below the temperature of the pipe and the exploiting device.

8. The device according to claim 7, wherein the means for lowering the pressure of the sampled gases are configured to maintain the pressure of the sampled gases in the pipe lower than a value such that the temperature of the sampled gases in the pipe remains higher than the dew point of the sampled gases in the pipe, considering the temperature of the pipe.

9. The device according to claim 7, wherein the expansion nozzle is a sonic nozzle.

10. The device according to claim 9, wherein the suction source has a suction power higher than a value such that the pressure of the sampled gases circulating in the pipe remains lower than one third of the pressure of the sampled gases upstream from the expansion nozzle, considering variations of the suction power when the suction power is not regulated.

11. The device according to claim 7, comprising means for regulating a suction power of the suction source to maintain the pressure of the sampled gases in the pipe substantially constant.

12. The device according to claim 7, wherein the probe comprises a filter for extracting solid particles in the sampled gases.

13. The device according to claim 7, comprising heating means for increasing the temperature in the pipe above the dew point of the sampled gases.

14. The device according to claim 7, wherein the suction source comprises a pump connected to the exploiting device through a pipe, so as to suck the gases in the pipe and in the exploiting device.

15. The device according to claim 7, wherein the exploiting device is a low pressure gas analyzer of the type based on cavity ring-down spectroscopy.

* * * * *

UNITED STATES PATENT AND TRADEMARK OFFICE
CERTIFICATE OF CORRECTION

PATENT NO. : 8,467,064 B2
APPLICATION NO. : 13/114093
DATED : June 18, 2013
INVENTOR(S) : Lonigro et al.

Page 1 of 1

It is certified that error appears in the above-identified patent and that said Letters Patent is hereby corrected as shown below:

In the Claims

In column 6, line 45, in Claim 7, after "from", delete "by", therefor

Signed and Sealed this
Thirteenth Day of August, 2013

Teresa Stanek Rea
*Acting Director of the United States Patent and Trademark Office*